(12) United States Patent
Nishimura

(10) Patent No.: US 9,977,236 B2
(45) Date of Patent: May 22, 2018

(54) OPTICAL SCANNING METHOD AND OPTICAL SCANNING APPARATUS

(71) Applicant: OLYMPUS CORPORATION, Tokyo (JP)

(72) Inventor: Junichi Nishimura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/655,350

(22) Filed: Jul. 20, 2017

(65) Prior Publication Data
US 2017/0322413 A1 Nov. 9, 2017

Related U.S. Application Data

(63) Continuation of application No. PCT/JP2015/000265, filed on Jan. 21, 2015.

(51) Int. Cl.
*G02B 26/10* (2006.01)
*G02B 23/24* (2006.01)
*A61B 1/00* (2006.01)

(52) U.S. Cl.
CPC ........ *G02B 26/101* (2013.01); *A61B 1/00165* (2013.01); *A61B 1/00172* (2013.01); *G02B 23/2469* (2013.01); *G02B 26/103* (2013.01)

(58) Field of Classification Search
CPC . G02B 26/101–26/103; G02B 23/2469; A61B 1/00172
See application file for complete search history.

(56) References Cited

U.S. PATENT DOCUMENTS

2009/0028407 A1* 1/2009 Seibel ................. A61B 1/0008
382/131

FOREIGN PATENT DOCUMENTS

| JP | S61-253481 | 11/1986 |
|----|------------|---------|
| JP | 2005-501279 A | 1/2005 |
| JP | 2009-516568 A | 4/2009 |
| JP | 2009-240621 | 10/2009 |
| JP | 2010-501246 A | 1/2010 |

OTHER PUBLICATIONS

English translation of International Preliminary Report on Patentability dated Aug. 3, 2017 together with the Written Opinion received in related International Application No. PCT/JP2015/000265.
International Search Report dated Apr. 7, 2015 issued in PCT/JP2015/000265.

* cited by examiner

*Primary Examiner* — Jerry Rahll
(74) *Attorney, Agent, or Firm* — Scully, Scott, Murphy & Presser, P.C.

(57) ABSTRACT

This optical scanning method yields a high quality image. An emission end of an optical fiber is displaced two-dimensionally to scan light emitted from the optical fiber, the emission end being displaced with an optical scanning actuator that includes a first driver and a second driver for driving the emission end in different directions. A circular scanning area is scanned by controlling, with a driver controller, a first drive signal supplied to the first driver and a second drive signal supplied to the second driver so as to rotate a scanning pattern of the light while causing the scanning pattern to reciprocate repeatedly in a nearly parallel manner with constant length.

6 Claims, 9 Drawing Sheets

OPTICAL SCANNING METHOD AND OPTICAL SCANNING APPARATUS

CROSS-REFERENCE TO RELATED APPLICATION

The present application is a Continuing Application based on International Application PCT/JP2015/000265 filed on Jan. 21, 2015, the entire disclosure of which is incorporated herein by reference.

TECHNICAL FIELD

This disclosure relates to an optical scanning method and to an optical scanning apparatus that implements this optical scanning method.

BACKGROUND

For example, a known scanning endoscope scans a test site by irradiating light from an optical fiber towards the test site while displacing the emission end of the optical fiber with an optical scanning actuator. This scanning endoscope then detects light that is reflected or scattered at the test site, fluorescent light that is generated at the test site, or other such light (for example, see JP 2010-501246 A (PTL 1)).

In addition to the observation mode for diagnosis, the scanning endoscope disclosed in PTL 1 can operate in many other modes for other purposes, such as a treatment mode. Therefore, as the method for scanning the test site, the method for scanning over the required scanning pattern can be selected from among a plurality of different scanning methods in which the scanning pattern may be a spiral pattern, raster pattern, Lissajous pattern, propeller pattern, or other pattern.

CITATION LIST

Patent Literature

PTL 1: JP 2010-501246 A

SUMMARY

An optical scanning method according to this disclosure is for displacing an emission end of an optical fiber two-dimensionally to scan light emitted from the optical fiber, the emission end being displaced with an optical scanning actuator that includes a first driver and a second driver configured to drive the emission end in different directions, the optical scanning method comprising:

scanning a circular scanning area by controlling, with a driver controller, a first drive signal supplied to the first driver and a second drive signal supplied to the second driver so as to rotate a scanning pattern of the light while causing the scanning pattern to reciprocate repeatedly in a nearly parallel manner with constant length.

The drive controller may rotate the scanning pattern in one direction by inverting a phase of the first drive signal at a rotation angle of the scanning pattern where a displacement of the emission end due to the first driver is minimized and inverting a phase of the second drive signal at a rotation angle of the scanning pattern where a displacement of the emission end due to the second driver is minimized.

The drive controller may rotate the scanning pattern back and forth over a range of 180° by inverting a phase of the first drive signal or the second drive signal at a rotation angle of the scanning pattern where a displacement of the emission end due to the first driver or the second driver is minimized.

The amplitude of the first drive signal or the second drive signal may be changed gradually around an inversion point of the phase of the first drive signal or the second drive signal.

An optical scanning apparatus according to this disclosure comprises:

an optical fiber with a displaceably supported emission end;

an optical scanning actuator comprising a first driver and a second driver configured to displace the emission end two-dimensionally;

a drive controller configured to control a first drive signal supplied to the first driver and a second drive signal supplied to the second driver; and an optical input interface configured to cause light from a light source to enter the optical fiber;

wherein the drive controller controls the first drive signal and the second drive signal to rotate a scanning pattern of the light emitted from the optical fiber while causing the scanning pattern to reciprocate repeatedly in a nearly parallel manner with constant length, so as to scan a circular scanning area.

DETAILED DESCRIPTION

In general, images for observation (diagnosis) are preferably generated by a scanning method that keeps the scanning density as constant as possible, because such images have good image quality with little distortion. Among the various scanning methods, however, a spiral scanning method has an increasingly higher scanning density closer to the center of the spiral, and a scanning method with a Lissajous pattern has a higher scanning density at the periphery. With a propeller-shaped scanning method, the scanning patterns cross near the center, nearly forming a figure eight. The density therefore increases near the center.

By contrast, a raster scanning method has a more even scanning density than the other scanning methods. Since the scanning pattern moves slowly in the sub-scanning direction, however, it takes time to acquire information on the center of the observational field of view. Also, with an optical scanning actuator that supports the emission end of an optical fiber at one end to allow the emission end to vibrate, it is difficult to move the scanning pattern linearly without rotation. Hence, distortion easily occurs in an image generated by a raster scanning method. These issues with the above-described scanning endoscope similarly occur for example in a projector that scans light from an optical fiber and projects an image.

Therefore, it would be helpful to provide an optical scanning method that yields a high quality image and an optical scanning apparatus that implements this optical scanning method.

The following describes an embodiment of the present disclosure with reference to the drawings.

Figure 1:
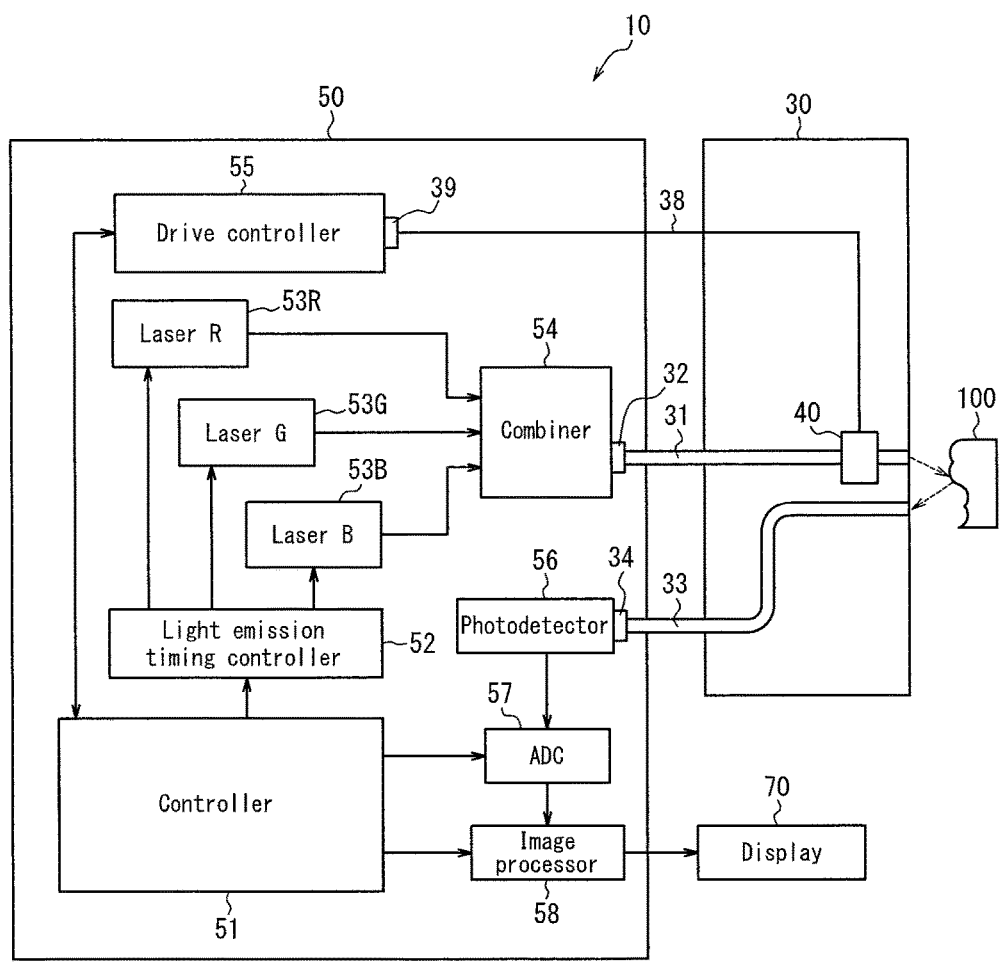
FIG. 1 schematically illustrates the configuration of the main part of an optical scanning apparatus according to an embodiment.

FIG. 1 schematically illustrates the configuration of the main part of an optical scanning apparatus according to one embodiment. The optical scanning apparatus according to this embodiment constitutes an optical scanning endoscope apparatus 10. The optical scanning endoscope apparatus 10 includes a scope (endoscope) 30, a control device body 50, and a display 70.

The control device body 50 includes a controller 51 that controls the optical scanning endoscope apparatus 10 overall, a light emission timing controller 52, lasers 53R, 53G, and 53B that constitute a light source, a combiner 54, and a drive controller 55. The laser 53R emits red laser light, the laser 53G emits green laser light, and the laser 53B emits blue laser light. Under the control of the controller 51, the light emission timing controller 52 controls the light emission timing of the three lasers 53R, 53G, and 53B. For example, Diode-Pumped Solid-State (DPSS) lasers or laser diodes may be used as the lasers 53R, 53G, and 53B. The laser light emitted from the lasers 53R, 53G, and 53B is combined by the combiner 54 and is incident as white illumination light on an optical fiber 31 for illumination, which is formed by a single-mode fiber. The combiner 54 may, for example, be configured to include a dichroic prism or the like. The configuration of the light source in the optical scanning endoscope apparatus 10 is not limited to this example. One laser light source may be used, or a plurality of other light sources may be used. The light source may be stored in a housing that is separate from the control device body 50 and is joined to the control device body 50 by a signal wire.

The optical fiber 31 for illumination extends to the tip of the scope 30. The incident end of the optical fiber 31 for illumination is coupled to an optical input interface 32 formed, for example, by an optical connector. The optical input interface 32 is detachably coupled to the combiner 54 and causes illumination light from the light source to enter the optical fiber 31 for illumination. The emission end of the optical fiber 31 for illumination is supported to allow vibration by the below-described optical scanning actuator. Illumination light entering the optical fiber 31 for illumination is guided to the tip of the scope 30 and irradiated towards an object (test site) 100. At this time, the drive controller 55 supplies a required drive signal to the optical scanning actuator and subjects the emission end of the optical fiber 31 for illumination to vibration driving. As a result, the object 100 is scanned in 2D by illumination light emitted from the optical fiber 31 for illumination. Details on this 2D scanning are provided below. Signal light, such as reflected light, scattered light, fluorescent light, and the like obtained from the object 100 by irradiation with illumination light is incident on the end face of an optical fiber bundle 33 for detection, which is formed by multi-mode fibers extending inside the scope 30. The signal light is then guided to the control device body 50.

The control device body 50 further includes a photodetector 56 for processing signal light, an analog/digital converter (ADC) 57, and an image processor 58. The photodetector 56 divides the signal light optically guided by the optical fiber bundle 33 for detection into spectral components and converts the spectral components into electric signals with a photodiode or the like. The emission end of the optical fiber bundle 33 for detection is coupled to an optical output interface 34 formed, for example, by an optical connector. The optical output interface 34 is detachably joined to the photodetector 56 and guides signal light from the object 100 to the photodetector 56. The ADC 57 converts the analog electric signals output from the photodetector 56 into digital signals and outputs the digital signals to the image processor 58.

On the basis of information such as the amplitude and phase of a drive signal supplied to the optical scanning actuator from the drive controller 55, the controller 51 calculates information on the scanning position along the scanning pattern of laser illumination light and provides the information to the image processor 58. The image processor 58 sequentially stores pixel data (pixel values) of the object 100 in a memory on the basis of the digital signals output by the ADC 57 and the scanning position information from the controller 51. After completion of scanning or during scanning, the image processor 58 generates an image of the object 100 by performing image processing, such as interpolation, as necessary and displays the image on the display 70.

In the above-described processes, the controller 51 synchronously controls the light emission timing controller 52, the photodetector 56, the drive controller 55, and the image processor 58.

Figure 2:
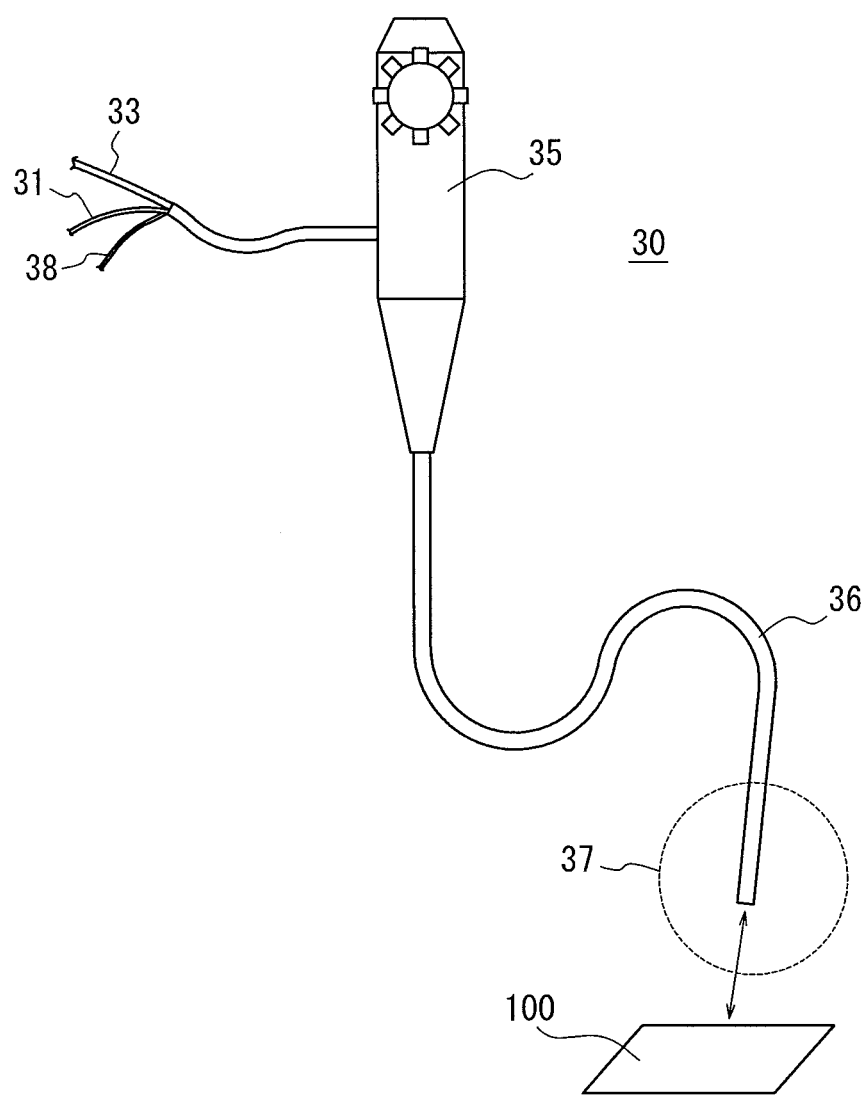
FIG. 2 is a schematic overview of the scope in FIG. 1.

FIG. 2 is a schematic overview of the scope 30. The scope 30 includes an operation part 35 and an insertion part 36. The optical fiber 31 for illumination and the optical fiber bundle 33 for detection are each detachably connected to the control device body 50 and extend from the operation part 35 to the tip 37 of the insertion part 36 (the portion indicated by the dashed line in FIG. 2). The scope 30 is also provided with wiring cables 38 that are connected to the optical scanning actuator and extend from the insertion part 36 through the operation part 35. The wiring cables 38 are connected detachably to the drive controller 55 via a connector 39, as illustrated in FIG. 1.

Figure 3:
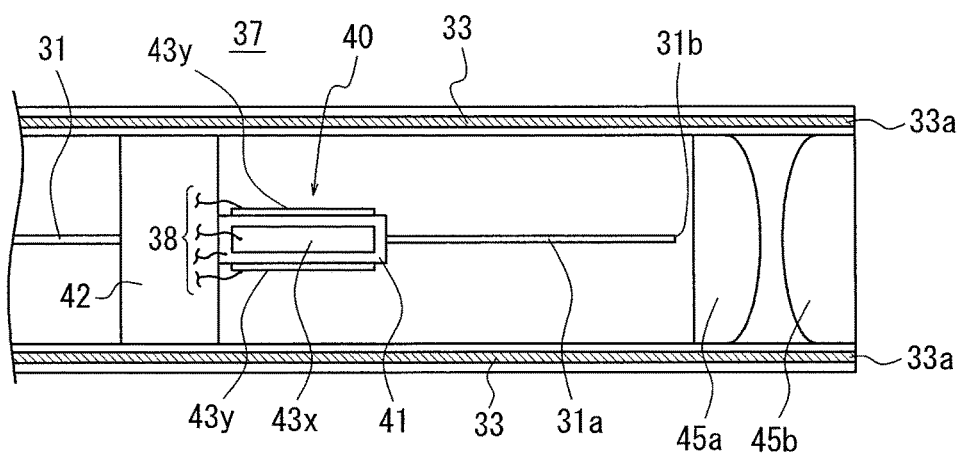
FIG. 3 is a cross-sectional diagram illustrating an enlargement of the tip of the scope in FIG. 2.

FIG. 3 is a cross-sectional diagram illustrating an enlargement of the tip 37 of the scope 30 in FIG. 2. An optical scanning actuator 40 and projection lenses 45a, 45b that constitute an illumination optical system are disposed at the tip 37. The optical scanning actuator 40 includes a ferrule 41. The ferrule 41 holds an emission end 31a of the optical fiber 31 for illumination, which passes through the ferrule 41. The optical fiber 31 for illumination is adhered to the ferrule 41. The end of the ferrule 41 opposite from an emission end face 31b of the optical fiber 31 for illumination is joined to a support 42 so that the ferrule 41 is supported at one end by the support 42 to allow oscillation. The optical fiber 31 for illumination extends through the support 42.

The ferrule 41 is, for example, made of a metal such as nickel. The ferrule 41 may be formed in any shape, such as a quadrangular prism or a cylinder. Piezoelectric elements $43x$ and $43y$ are mounted on the ferrule 41 by adhesive or the like to oppose each other in the x-direction and the y-direction, where the x-direction and y-direction are orthogonal to each other in a plane orthogonal to the z-direction, and the z-direction is a direction parallel to the optical axis direction of the optical fiber 31 for illumination. The piezoelectric elements $43x$ and $43y$ are rectangular, with the long sides in the z-direction. The piezoelectric elements $43x$ and $43y$ each have an electrode formed on both surfaces in the thickness direction and are each configured to be capable of expanding and contracting in the z-direction upon voltage being applied in the thickness direction via the opposing electrodes. The two piezoelectric elements 43x that oppose each other in the x-direction (only one piezoelectric element 43x being illustrated in FIG. 3) for example constitute the first driver, and the two piezoelectric elements 43y that oppose each other in the y-direction for example constitute the second driver.

Corresponding wiring cables 38 are connected to the electrode surfaces of the piezoelectric elements 43x and 43y opposite the electrode surfaces adhered to the ferrule 41. Similarly, corresponding wiring cables 38 are connected to the ferrule 41, which acts as a common electrode for the piezoelectric elements 43x and 43y. To the two piezoelectric elements 43x opposite each other in the x-direction, in-phase alternating voltage is applied as the first drive signal from the drive controller 55 illustrated in FIG. 1 through the corresponding wiring cables 38. Similarly, to the two piezoelectric elements 43y opposite each other in the y-direction, in-phase alternating voltage is applied as the second drive signal from the drive controller 55 through the corresponding wiring cables 38.

With this configuration, when one of the two piezoelectric elements 43x expands, the other contracts, causing the ferrule 41 to vibrate by bending in the x-direction. Similarly, when one of the two piezoelectric elements 43y expands, the other contracts, causing the ferrule 41 to vibrate by bending in the y-direction. As a result, the x-direction vibration and y-direction vibration are combined, so that the ferrule 41 is deflected integrally with the emission end 31a of the optical fiber 31 for illumination. Accordingly, upon illumination light entering the optical fiber 31 for illumination, the object of observation can be scanned in 2D by the illumination light emitted from the emission end face 31b.

The optical fiber bundle 33 for detection is disposed to pass through the peripheral portion of the insertion part 36 and extend to the end of the tip 37. A non-illustrated detection lens may also be disposed at the tip 33a of each fiber in the optical fiber bundle 33 for detection.

The projection lenses 45a, 45b are disposed at the extreme end of the tip 37. The projection lenses 45a, 45b are configured so that laser light emitted from an emission end face 31b of the optical fiber 31 for illumination is concentrated on a predetermined focal position. When detection lenses are disposed at the tip 33a of the optical fiber bundle 33 for detection, the detection lenses are disposed so that light that is reflected, scattered, or refracted by the object 100 (light that interacts with the object 100), fluorescent light, or other light resulting from laser light being irradiated on the object 100 is captured as signal light, concentrated on the optical fiber bundle 33 for detection, and combined. The projection lenses are not limited to a double lens structure and may be configured as a single lens or as three or more lenses.

Next, the scanning method by the optical scanning endoscope apparatus 10 according to this embodiment is described.

Figure 4:
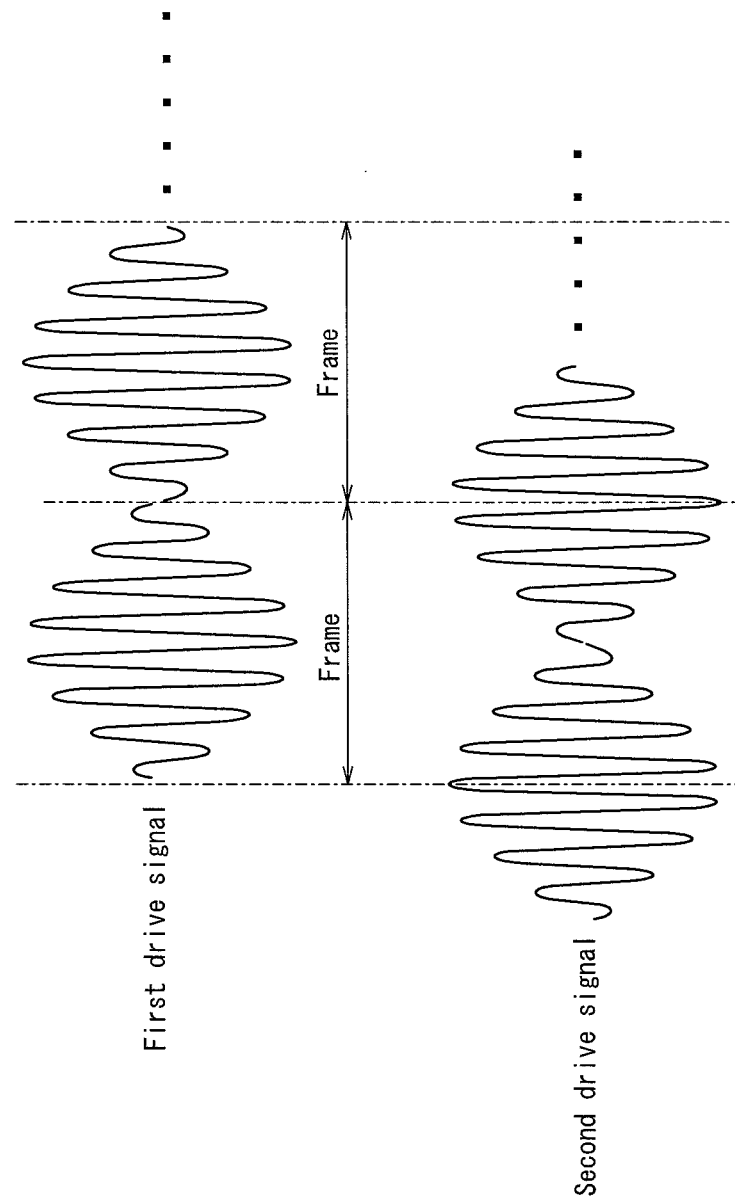
FIG. 4 is a waveform diagram of an example of the first drive signal and the second drive signal supplied to the optical scanning actuator in FIG. 3.

FIG. 4 is a waveform diagram of an example of the first drive signal and the second drive signal supplied to the optical scanning actuator 40 from the drive controller 55. The frequency of the first drive signal and the second drive signal is, for example, set at or near the frequency of the vibrated portion, which includes the emission end 31a of the optical fiber 31 for illumination that is driven by the optical scanning actuator 40. The first drive signal and the second drive signal are both set to nearly the same phase difference. The first drive signal and the second drive signal are modulated by a modulation signal with a sinusoidal amplitude and have an equivalent maximum amplitude. The phase difference between the amplitude modulation signals of the first drive signal and the second drive signal, i.e. the phase difference of the envelopes of the two signals, is 90°.

Figure 5:
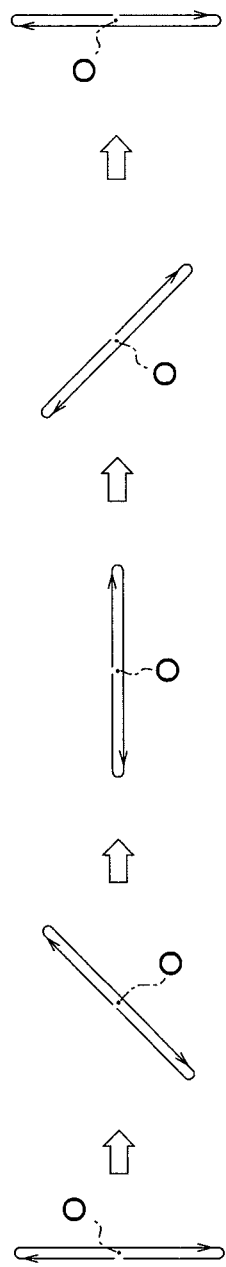
FIG. 5 schematically illustrates the scanning pattern.

Upon the optical scanning actuator 40 being driven by the first drive signal and the second drive signal illustrated in FIG. 4, the scanning pattern of light emitted from the optical fiber 31 for illumination rotates while reciprocating repeatedly in a nearly parallel manner with a constant length. In other words, as schematically illustrated in FIG. 5, one reciprocal movement of the scanning pattern can be regarded as a bar shape composed of an outgoing path in which the pattern moves in one direction and a return path in which the pattern moves nearly in parallel in the opposite direction, with the optical axis O when the optical fiber 31 for illumination is at rest lying between the paths. This bar-shaped scanning pattern rotates about the optical axis O with an equivalent length from the optical axis O to each of the turn-back points of the pattern.

Figure 6:
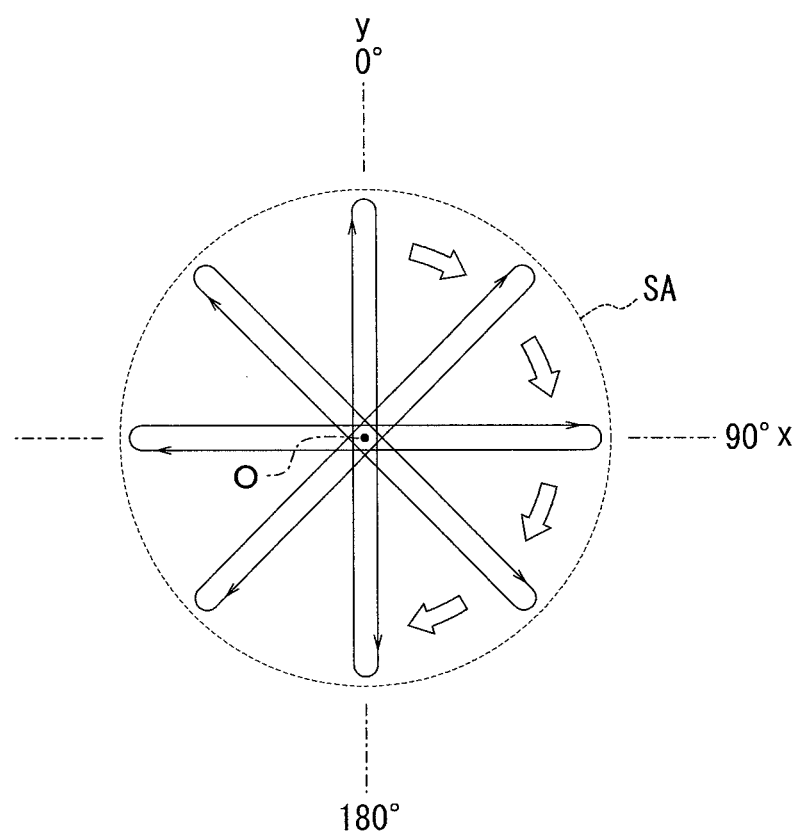
FIG. 6 illustrates the scanning area.

Therefore, as illustrated in FIG. 6, upon the rod-shaped scanning pattern rotating 180°, the pattern traced by the turn-back points at both ends of the rod forms a circle centered on the optical axis O, allowing the scanning area SA within this circle to be scanned. In this embodiment, the period during which the rod-shaped scanning pattern rotates 180° is taken as one frame period of an image, and an image of the object 100 is generated in the image processor 58.

In this embodiment, the phase of the first drive signal is inverted, as illustrated in FIG. 4, at the rotation angle of the rod-shaped scanning pattern where the displacement, due to the piezoelectric elements 43x, of the emission end 31a of the optical fiber 31 for illumination is minimized. In other words, as illustrated in FIG. 6, the phase of the first drive signal is inverted every 180° starting at 0°, i.e. every frame, where the horizontal direction is the x-direction, the vertical direction is the y-direction, the rotation angle when the rod-shaped scanning pattern is vertical is 0°, and the rotation angle when the rod-shaped scanning pattern is horizontal is 90°. Similarly, the phase of the second drive signal is inverted, as illustrated in FIG. 4, at the rotation angle of the rod-shaped scanning pattern where the displacement, due to the piezoelectric elements 43y, of the emission end 31a of the optical fiber 31 for illumination is minimized. In other words, in FIG. 6, the phase of the second drive signal is inverted every 180° starting at 90°, i.e. in the middle of a frame. As a result, the rod-shaped scanning pattern is rotated in one direction (clockwise in FIG. 6), and a one-frame image is generated every time the rod-shaped scanning pattern rotates 180°.

According to this embodiment, the rod-shaped scanning pattern with a constant length is composed of a nearly parallel outgoing path and a return path on either side of the center (optical axis O) of the circular scanning area SA, without passing through the center. The scanning area SA is repeatedly scanned over this scanning pattern while the rotation angle of the scanning pattern is changed, thereby allowing a good quality image with little variation in the scanning density and little distortion to be generated. The scanning speed becomes constant over the entire scanning area SA, yielding a clear image with uniform image quality. Furthermore, with the first drive signal and the second drive signal, the optical scanning actuator 40 repeats the operation of causing the emission end 31a of the optical fiber 31 for illumination to reciprocate along the diameter, thereby also easily allowing the emission end 31a to be driven at or near the resonance frequency.

The drive controller 55 inverts the phase of the first drive signal and of the second drive signal at the rotation angle of the rod-shaped scanning pattern where the respective displacements, due to the piezoelectric elements 43x and 43y, of the emission end 31a of the optical fiber 31 for illumination are minimized. The rod-shaped scanning pattern is thereby rotated in one direction. Accordingly, with simple control, a seamless image can be continuously and smoothly generated with the optical fiber 31 for illumination that is supported at one end.

Figure 7:
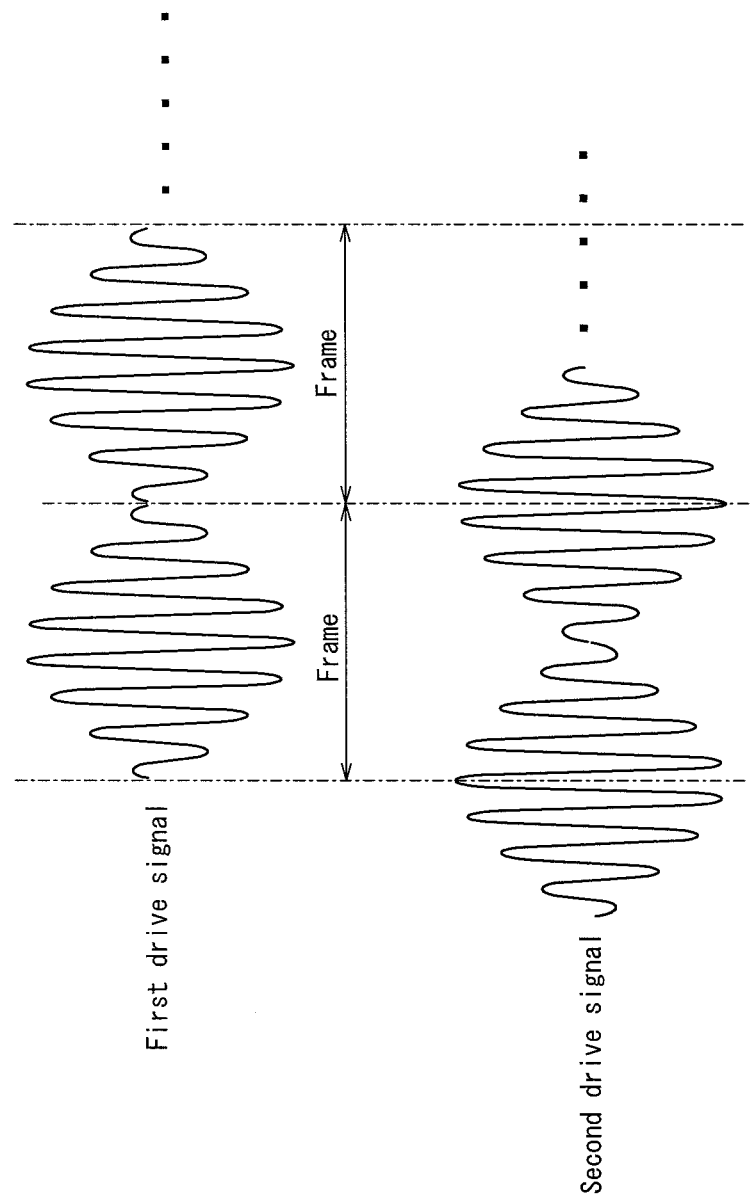
FIG. 7 is a waveform diagram of an example of the first drive signal and the second drive signal in a modification.
Figure 8:
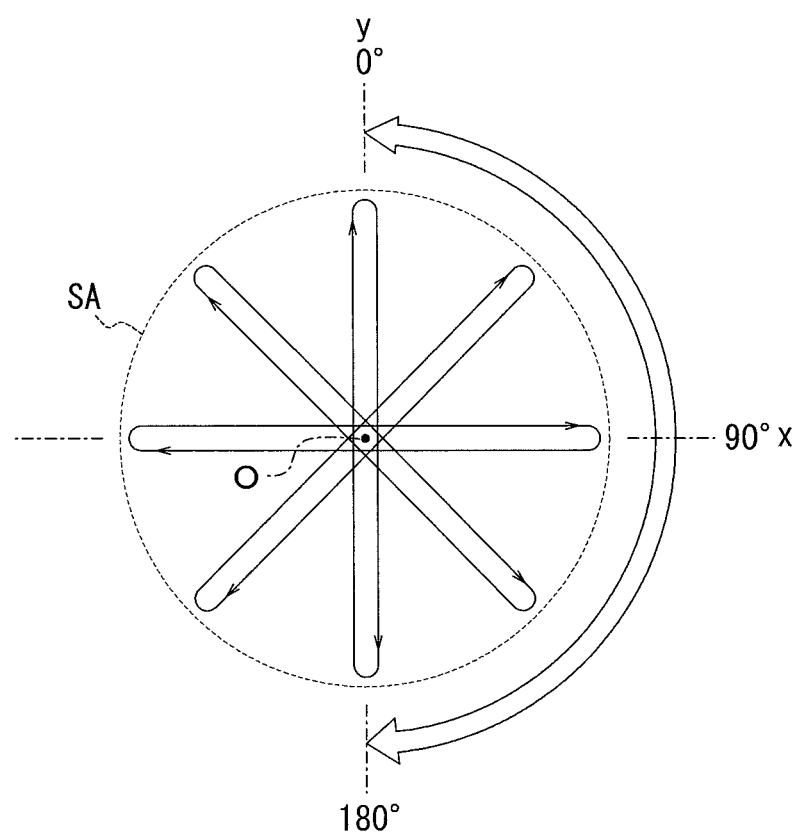
FIG. 8 illustrates the modification in FIG. 7.

This disclosure is not limited to the above embodiments, and a variety of changes and modifications may be made. For example, the drive controller 55 may be configured to invert only the phase of either the first drive signal or the second drive signal, such as only the second drive signal as illustrated in FIG. 7, at the rotation angle of the rod-shaped scanning pattern where the displacement of the emission end 31a of the optical fiber 31 for illumination is minimized. With this approach, as illustrated in FIG. 8, a circular scanning area SA can be scanned by rotating the rod-shaped scanning pattern back and forth over a range of 180°. In this case as well, a good quality image can be generated.

Figure 9:
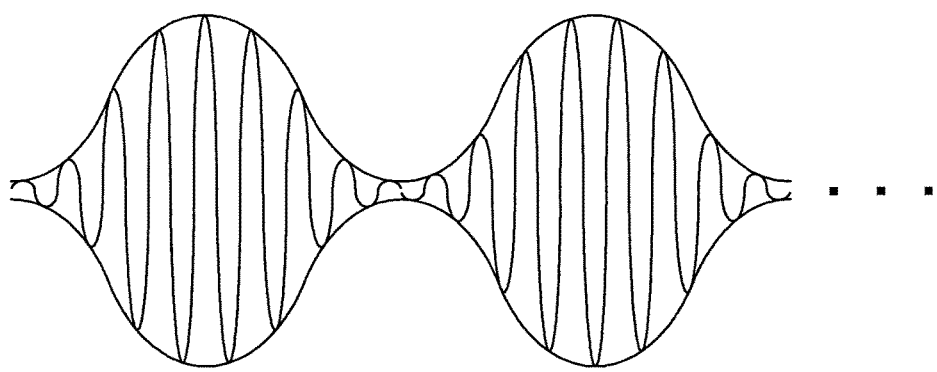
FIG. 9 illustrates another modification.

In the above embodiments and modifications, when inverting the phase of the drive signals, the amplitude of the drive signal for inverting the phase may be changed gradually around the inversion point. In other words, the envelope of the drive signal for inverting the phase may be changed smoothly, as illustrated in FIG. 9. With this approach, images can be generated more smoothly.

The first driver and second driver of the optical scanning actuator 40 are not limited to the piezoelectric method using piezoelectric elements. This disclosure may be effectively applied also when using another known driving method, such as an electromagnetic method that uses coils and a permanent magnet. In the optical scanning endoscope apparatus 10 illustrated in FIG. 1, the controller 51 and drive controller 55 are illustrated separately, but the controller 51 may include the functions of the drive controller 55. Furthermore, this disclosure is not limited to an optical scanning endoscope apparatus and may also be adopted in an optical scanning microscope or an optical scanning projector.

The invention claimed is:

1. An optical scanning apparatus comprising:
   an optical fiber with a displaceably supported emission end;
   an optical scanning actuator comprising a first driver and a second driver configured to displace the emission end two-dimensionally;
   a drive controller configured to control a first drive signal supplied to the first driver and a second drive signal supplied to the second driver; and
   an optical input interface configured to cause light from a light source to enter the optical fiber,
   wherein the drive controller is configured to control the first drive signal and the second drive signal to rotate a rod-shaped scanning pattern of the light, wherein the rod-shaped scanning pattern has a constant length and includes an outgoing path in a first direction along the length axis of the rod-shaped scanning pattern, a return path in a second direction along the length axis of the rod-shaped scanning pattern, and turn-back points connecting the outgoing path and the return path, so as to scan a circular scanning area, and
   wherein the drive controller is configured to rotate the rod-shaped scanning pattern back and forth over a range of 180° by inverting a phase of the first drive signal or the second drive signal at a rotation angle of the rod-shaped scanning pattern where a displacement of the emission end due to the first driver or the second driver is minimized.

2. An optical scanning method for displacing an emission end of an optical fiber two-dimensionally to scan light emitted from the optical fiber, the emission end being displaced with an optical scanning actuator that includes a first driver and a second driver configured to drive the emission end in different directions, the optical scanning method comprising:
   scanning a circular scanning area by controlling, with a drive controller, a first drive signal supplied to the first driver and a second drive signal supplied to the second driver so as to rotate a rod-shaped scanning pattern of the light, wherein the rod-shaped scanning pattern has a constant length and includes an outgoing path in a first direction along the length axis of the rod-shaped scanning pattern, a return path in a second direction along the length axis of the rod-shaped scanning pattern, and turn-back points connecting the outgoing path and the return path,
   wherein the drive controller rotates the rod-shaped scanning pattern in one direction by inverting a phase of the first drive signal at a rotation angle of the rod-shaped scanning pattern where a displacement of the emission end due to the first driver is minimized and inverting a phase of the second drive signal at a rotation angle of the rod-shaped scanning pattern where a displacement of the emission end due to the second driver is minimized.

3. The optical scanning method of claim 2,
   wherein an amplitude of the first drive signal or the second drive signal is changed gradually around an inversion point of the phase of the first drive signal or the second drive signal.

4. An optical scanning method for displacing an emission end of an optical fiber two-dimensionally to scan light emitted from the optical fiber, the emission end being displaced with an optical scanning actuator that includes a first driver and a second driver configured to drive the emission end in different directions, the optical scanning method comprising:
   scanning a circular scanning area by controlling, with a drive controller, a first drive signal supplied to the first driver and a second drive signal supplied to the second driver so as to rotate a rod-shaped scanning pattern of the light, wherein the rod-shaped scanning pattern has a constant length and includes an outgoing path in a first direction along the length axis of the rod-shaped scanning pattern, a return path in a second direction along the length axis of the rod-shaped scanning pattern, and turn-back points connecting the outgoing path and the return path,
   wherein the drive controller rotates the rod-shaped scanning pattern back and forth over a range of 180° by inverting a phase of the first drive signal or the second drive signal at a rotation angle of the rod-shaped scanning pattern where a displacement of the emission end due to the first driver or the second driver is minimized.

5. The optical scanning method of claim 4,
   wherein an amplitude of the first drive signal or the second drive signal is changed gradually around an inversion point of the phase of the first drive signal or the second drive signal.

6. An optical scanning apparatus comprising:
- an optical fiber with a displaceably supported emission end;
- an optical scanning actuator comprising a first driver and a second driver configured to displace the emission end two-dimensionally;
- a drive controller configured to control a first drive signal supplied to the first driver and a second drive signal supplied to the second driver; and
- an optical input interface configured to cause light from a light source to enter the optical fiber,
- wherein the drive controller is configured to control the first drive signal and the second drive signal to rotate a rod-shaped scanning pattern of the light emitted from the optical fiber, wherein the rod-shaped scanning pattern has a constant length and includes an outgoing path in a first direction along the length axis of the rod-shaped scanning pattern, a return path in a second direction along the length axis of the rod-shaped scanning pattern, and turn-back points connecting the outgoing path and the return path, so as to scan a circular scanning area, and
- wherein the drive controller is configured to rotate the rod-shaped scanning pattern in one direction by inverting a phase of the first drive signal at a rotation angle of the rod-shaped scanning pattern where a displacement of the emission end due to the first driver is minimized and inverting a phase of the second drive signal at a rotation angle of the rod-shaped scanning pattern where a displacement of the emission end due to the second driver is minimized.

* * * * *